United States Patent [19]

Yanagisawa et al.

[11] 4,048,155
[45] Sept. 13, 1977

[54] PROCESS FOR PREPARING 7 α-ALKOXYCEPHALOSPORIN DERIVATIVES

[75] Inventors: Hiroaki Yanagisawa; Akiko Ando; Masami Fukushima; Hideo Nakao, all of Tokyo, Japan

[73] Assignee: Sankyo Company Limited, Tokyo, Japan

[21] Appl. No.: 627,111

[22] Filed: Oct. 30, 1975

[30] Foreign Application Priority Data

Nov. 15, 1974 Japan .............................. 49-131761

[51] Int. Cl.$^2$ .................. C07D 501/18; C07D 501/36
[52] U.S. Cl. .................................................. 542/422
[58] Field of Search ....................... 260/243 C, 240 G

[56] References Cited

U.S. PATENT DOCUMENTS

| 3,775,410 | 11/1973 | Christensen et al. | 260/243 C |
| 3,840,532 | 10/1974 | Hayes et al. | 260/243 C |
| 3,875,146 | 4/1975 | Christensen et al. | 260/243 C |

Primary Examiner—Nicholas S. Rizzo
Assistant Examiner—David E. Wheeler
Attorney, Agent, or Firm—Flynn & Frishauf

[57] ABSTRACT

A process for introducing an alkoxy group into the 7α-position of a 7-amino-3-cephem-4-carboxylic acid derivative which comprises oxidizing a salt of 7-benzylideneamino-3-cephem-4-carboxylic acid derivative and reacting the product with an alkanol.

The 7α-alkoxy-3-cephem-4-carboxylic acid derivatives obtained by the present invention are useful as intermediates for the synthesis of antibacterial agents.

7 Claims, No Drawings

PROCESS FOR PREPARING 7 α-ALKOXYCEPHALOSPORIN DERIVATIVES

This invention relates to a novel process for introducing an alkoxy group into the 7α-position of 7-amino-3-cepehm-4-carboxylic acid derivative.

More particularly, this invention relates to a process for the preparation of 7α-alkoxy-3-cephem-4-carboxylic acid derivatives having the formula

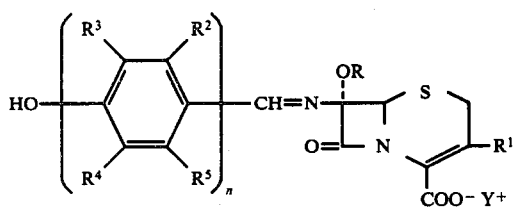

(I)

wherein R represents an alkyl group having 1–4 carbon atoms, $R^1$ represents hydrogen atom, methyl group, cyanomethyl group, an acyloxymethyl group, carbamoyloxymethyl group, an alkoxymethyl group, an alkylthiomethyl group or a heterocyclic thiomethyl group, $R^2$, $R^3$, $R^4$ and $R^5$ may be the same or different and each represents hydrogen atom, an alkyl group having 1–4 carbon atoms, an alkoxy group having 1–4 carbon atoms, a halogen atom, cyano group or a alkoxycarbonyl group having 1–4 carbon atoms in the alkoxy moiety, or $R^2$ and $R^3$ or $R^4$ and $R^5$ may be linked together to form a saturated, unsaturated or aromatic ring, n is an integer of 1 or 2 and Y+ is a cation.

In the above formula (I), R is preferably a methyl group. $R^1$ is preferably a hydrogen atom; methyl group; cyanomethyl group; an acyloxymethyl group such as an alkanoyloxymethyl group, e.g., acetoxymethyl, propionyloxymethyl, pivaloyloxymethyl or an aroyloxymethyl group, e.g., benzoyloxymethyl; carbamoyloxymethyl group; an alkoxymethyl group such as methoxymethyl, ethoxymethyl and butyloxymethyl; an alkylthiomethyl group such as methylthiomethyl, ethylthiomethyl, propylthiomethyl; or a heterocyclic thiomethyl group such as 2-pyridylthiomethyl, 1-methyl-1H-tetrazol-5-ylthiomethyl, 2-(1,3,5-triazolo)thiomethyl, 3-pyrazolothiomethyl, 1-imidazolinylthiomethyl, 5-methyl-1,3,4-thiadiaolyl-2-thiomethyl. The groups $R^2$ to $R^5$ may be the same of different and each represents preferably a hydrogen atom; a straight or branched alkyl group having 1–4 carbon atoms such as methyl, ethyl, propyl, isopropyl and tert.-butyl; a straight or branched alkoxy group having 1–4 carbon atoms such as methoxy, ethoxy, propoxy, isopropoxy and tert.-butoxy; a halogen atom such as chlorine and bromine; cyano group; an alkoxycarbonyl group having 1–4 carbon atoms in the alkyl moiety such as methoxycarbonyl, ethoxycarbonyl and tert.-butoxycarbonyl. $R^2$ and $R^3$ or $R^4$ and $R^5$ may be linked together to form a saturated, unsaturated or aromatic ring such as cyclopentane, cyclohexane, cycloheptane and benzene. n is an integer of 1 or 2 and; when n is 2, for example, biphenyl, binaphthalene or p-(4-napthyl)benzene may be formed. $R^3$ and $R^4$ may be suitably selected from a sterically hindered alkyl group such as isopropyl and tert.-butyl. Y+ is a cation suitably selected from the group consisting of an alkali metal ion and an ammonium ion having the formula

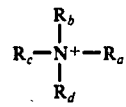

wherein $R_a$, $R_b$, $R_c$ and $R_d$ may be the same or different and each represents hydrogen atom; a straight or branched alkyl group having 1-8 carbon atoms such as methyl, ethyl, propyl, isopropyl, tert.-butyl, octyl and tert.-octyl; a cycloalkyl group having 5-7 carbon atoms such as cyclopentyl, cyclohexyl and cycloheptyl; phenyl group; or a phenylalkyl group having 1-4 carbon atoms in the alkyl moiety such as benzyl or phenethyl; or $R_a$ and $R_b$ may be linked together with N to form a saturated heterocyclic ring such as pyrrolidine, piperidine and morpholine; or $R_a$, $R_b$ and $R_c$ may be linked together with N to form a heteroaromatic ring such as pyridine, picoline, lutidine, quinoline, quinaldine and pyrimidine.

The most preferable cations as Y+ are lithium, sodium, tert.-butylammonium, tert.-octylammonium, dicyclohexylammonium, diisopropylammonium, triethylammonium and trimethylbenzylammonium ions.

As the method for introducing an alkoxy group into the 7α-position of the cephem nucleus, there have heretofore been known (a) a method comprising diazotizing 7-aminocephalosporanic acid and converting the 7-position substituent to an alkoxy group (Japanese Pat. Pro. Pub. 931/72), (b) a method comprising reacting a 7-benzylideneamino compound wih a dialkyl peroxide or the like (Japanese Pat. Pro. Pub. 42691/72), (c) a method comprising alkylthionating or fluorinating and acylating a 7-banzylideneamino compound and converting the 7-position substituent to an alkoxy group [J. O. C. 38 943 and 2857, (1973)], (d) a method comprising N-chlorinating the 7-acylamino group, converting the N-chlorinated group to an acylimino group and adding methanol thereto [J. A. C. S. 95 2403, (1973)], etc. Each of these known methods, however, involves problems of difficulties. As a result of our research in this field, we have developed the industrially excellent process of this invention.

Compounds represented by the above formula (I), which are prepared according to the process of this invention, are novel compounds and are valuable intermediates to be used for the preparation of cephalosporin compounds having an alkoxy group at the 7α-position. For example, when a compound represented by the above formula (I) is treated with a hydrazine compound to split off the benzylidene group at the 7-position, the amino group at the 7-position is acylated and then the acylated compound is contacted with an acid to convert a free carboxyl acid, a cephalosporin compound valuable as a medicine can be prepared. Accordingly, 7α-alkoxycephalosporin compounds can be prepared very easily with commercial and industrial advantages through the intended products of this invention by utilizing the process of this invention.

According to the process of this invention, compounds represented by the above formula (I) can be prepared by oxidizing a 7-benzylideneamino-3-cephem-4- carboxylic acid derivative having the formula

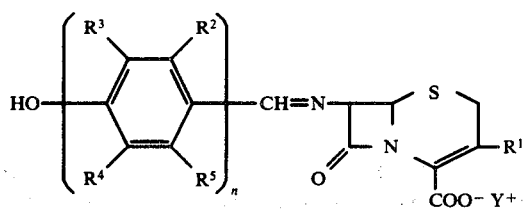

(II)

wherein R¹, R², R³, R⁴, R⁵, n and Y⁺ are as defined above and reacting the resulting product with an alkanol having 1-4 carbon atoms. In carrying out the process of this invention, the oxidation step may be conducted by contacting the compound (II) with an oxidizing agent in an appropriate solvent. In the oxidizing agent there is no particular limitation if it can convert the phenol moiety in the benzylidene group into the corresponding quinoid form without any attack to the cephem nucleus. Representative examples of such an oxidizing agent include a metal oxide such as lead dioxide and manganese dioxide, a quinone derivative with a powerful oxidizing property such as dicyanodichlorbenzoquinone, a hypochlorite derivative such as tert.-butylhypochlorite in the presence of a base which produces a phenolate ion, or a halogen compound which possesses oxidizing power such as N-bormosuccinimide and N-chlorsuccinimide. As the solvent, the may be employed an aromatic hydrocarbon such as benzene and toluene, a halogenated hydrocarbon such as chloroform and methylene chloride and an ether such as dioxane and tetrahydrofuran. The reaction may proceed in a stoichiometric amount of an oxidizing agent, but an excess amount of the reagent of about 1.1-10 times molar may be usually used for acceleration of the reaction. The reaction temperature is not particularly critical and the reaction may be usually effected at room temperature, but the reaction may proceed at a higher or lower temperature. The time required for the reaction may be varied mainly depending upon the starting material, the oxidizing agent, the sort of solvent, the reaction temperature, and the like, but it may usually take about 10 minutes to several tens of minutes. The compound having the above-described general formula (II) which may be employed in the process of this invention may be prepared in situ by the interaction of a 7-aminocephalosporin compound with an aryl aldehyde prior to the practice of the process of this invention and used per se. The product formed by the oxidation may be recovered in a usual manner. For instance, the oxidizing agent is separated by filtration from the reaction mixture and the solvent is removed from the filtrate under a reduced pressure to give the product, which may be purified by a conventional method, e.g., column chromatography, but the filtrate per se may be employed without isolation and purification of the product as a solution of the starting material in the subsequent step according to the process of his invention.

The alkoxylation step may be easily conducted by contacting the product obtained above with the alkanol. Representative examples of the alcohol include methanol, ethanol and propanol. The reaction may proceed in a stoichiometric amount of the alkanol, but an excess amount of the alkanol of about 10-100 times molar may be usually used for the promotion of the reaction. The rection temperature is not particularly critical and the reaction may be usually carried out at room temperature, but the reaction may proceed at a higher or lower temperature. The time required for the reaction may be varied mainly depending upon the starting material, the kind of lower alkanol, the reaction temperature, and the like, but it may usually take about 0.5 to several hours. Except in the case where as an oxidizing agent there is used a metal oxide which can be easily removed from the reaction mixture after the reaction is finished, the two steps in this invention can be preferably carried out simultaneously by reacting with an oxidizing agent in the presence of the alkanol.

In this case, the reaction may be easily carried out by the following procedure. To a solution of the compound having the above-mentioned general formula (II) in a suitable solvent is added the lower alknaol employed in the reaction and subsequently adding the oxidizing agent, for instance, dicyanodichlorbenzoquinone or tert.-butylhypochlorite in the presence of a base. As to the solvent which may be employed in this reaction there is no particular limitation if it will not participate in the reaction and various inert organic solvents may be used. As examples of such solvents may be mentioned, for instance, ether, tetrahydrofuran and the like. The lower alkanol which is employed for the alkoxylation reaction may be also used as a solvent. The oxidizing agent may be preferably used in a stoichiometric or a slight excess amount, and in case of using a halogenated compound as an oxidizing agent in equimolar of an appropriate base is additionally used.

The base which is employed in the reaction is a basic metal compound or a basic nitrogen compounds. As examples of basic metal compounds may be exemplified, for instance, alkoxides such as lithium methoxide and the like.

As examples of basic nitrogen compounds may be mentioned various kinds of amines, among which tert.-amines, for instance, DBU (1,8 -diazabicyclo [5.4.0]-7-undecene) may be preferably used. Alkali metal alkoxides may be preferably used.

As to the reaction temperature there is no particular limitation, but, in order to minimize occurrence of side reactions, a relatively low temperature may be preferable and the reaction may be preferably conducted under a room temperature or most preferably under 0° C. The time required for the reaction may be varied mainly depending upon the sort of oxidizing agent, the sort of alcohol and the reaction temperature employed and the like, but it may usually take several minutes to several tens of minutes.

The alkoxylated compound may be recovered from the reaction mixture in a usual manner. For instance, the solvent and excess alkanol are removed from the reaction mixture to give an amorphous end product in this step, which may be then purified by conventional method, e.g., by recrystallization or column chromatography.

The starting material in the process of this invention as illustrated in the above formula (II) is novel and can be prepared by the following way;

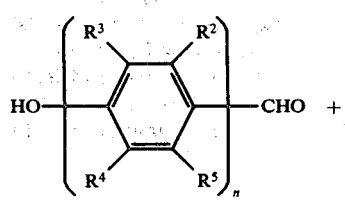

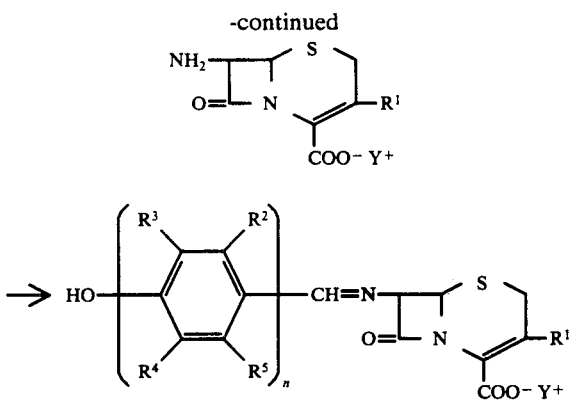

Rhu 1 to $R^5$, n and $Y^+$ in the above formulae are the same as defined above.

The reaction can be carried out by conventional means and will be exemplified later.

This invention will be illustrated in detail by the following examples and referential examples, but these are not to be construed as limiting the scope of the invention.

REFERENTIAL EXAMPLE 1

Dicyclohexylammonium 7β-(4-hydroxy-3,5-di-tert.-butylbenzylideneamino)-3-acetoxymethyl-3-cephem-4-carboxylate To a suspension of 29.2g of 7-amino-3-acetoxymethyl-3-cephem-4-carboxylic acid in 600 ml of methanol, 18.1g of dicyclohexylamine was added. The mixture was stirred for 1 hour at room temperature. To a semi-transparent solution thus obtained was added 24.0g of 4-hydroxy-3,5-di-tert.-butylbenzaldehyde and stirred for 2 hours at room temperature. Stirring was further continued for 5 hours after addition of 50g of molecular sieve 3A. The reaction mixture was filtered and the filtrate was condensed under a reduced pressure to give a crystalline substance, which, after addition of isopropanol, was collected by filtration affording 45.03g of the desired product as white crystals melting at 183°–185° C with decomposition.

UV spectrum $\lambda_{max}^{THF}$ 280 nm
NMR spectrum (CDCl$_3$) δ ppm:
8.53 (singlet, —CH=N—)
7.66 (singlet, benzene ring-H)
5.60 (broad, OH)
5.37 (doublet, H at 7-position)
5.19 (doublet, H at 6-position)
5.05 (doublet of doublet, —CH$_2$— at 3-position)
3.40 (doublet of doublet, H$_2$ at 2-position)
2.07 (singlet, CH$_3$CO)
1.50 (singlet, C(CH$_3$)$_3$)

Thin layer chromatography (silica gel):
Developing solvent: chloroform:methanol=4:1
$R_f$ = 0.71

| | Elementary analysis for $C_{37}H_{55}N_3O_6S$ | | | |
|---|---|---|---|---|
| | C | H | N | S |
| Calculated: | 66.35; | 8.28; | 6.27; | 4.79 |
| Found: | 66.60; | 8.44; | 6.20; | 4.65 |

REFERENTIAL EXAMPLE 2

Lithium 7β-(4-hydroxy-3,5-di-tert.-butylbenzylidene-amino)-3-methyl-3-cephem-4-carboxylate To a suspension of 430 mg of 7β-amino-3-methyl-3-cemphem-4-carboxylic acid in 6 ml of methanol was dropwise added a solution of 14 mg of lithium in 2 ml of methanol under stirring, and subsequently a solution of 470 mg of 4-hydroxy-3,5-di-tert.-butylbenzaldehyde and 4 ml of chloroform was added. After the resulting mixture was stirred overnight at room temperature, the insoluble substance which formed was removed by filtration from the reaction mixture and the solvent ws completely removed from the filtrate at room temperature to leave the desired product as a yellow powder.

Thin layer chromatography (silica gel):
Developing solvent: chloroform:methanol=4:1
$R_f$ = 0.50

REFERENTIAL EXAMPLE 3

Trimethylbenzylammonium 7β-(4-hydroxy-3,5-di-tert.-butylbenzylideneamino)-3-(1-methyl-1H-tetrazol-5-yl)thiomethyl-3-cephem-4-carboxylate To a mixture of 8 ml of methanol and 13 ml of tetrahydrofuran was added 984 mg of 7-amino-3-(1-methyl-1H-tetrazol-5-yl) thiomethyl-3-cephem-4-carboxylic acid and under stirring and ice-cooling 1.36 ml of 40% methanolic solution of triton B (trimethylbenzylammonium hydroxide) was added. After the mixture reached room temperature and became a homogeneous solution, 712 mg of 4-hydroxy-3,5-di-tert.-butylbenzaldehyde and 2g of anhydrous calcium sulfate were added to the solution and the resulting mixture was stirred overnight at room temperature. After filtration of the reaction mixture, the filtrate was condensed to give the desired Schiff's base as a pale brown powder in a quantitative yield.

Thin layer chromatography (silica gel):
Developing solvent: chlorform:methanol=3:1
$R_f$ = 0.50

EXAMPLE 1

Dicyclohexylammonium 7α-methyoxy-7β-(4-hydroxy-3,5-di-tert.-butylbenzylideneamino)-3-acetoxymethyl-3-cephem-4-carboxylate A solution of 13.4g of dicyclohexylammonium 7β-(4-hydroxy-3,5-di-tert.-butylbenzylideneamino)-3-acetoxymethyl-3-cephem-4-carboxylate in 200 ml of methanol was cooled to −15° C and a solution of 4.74g of 2,3-dichloro-5,6-dicyano-1,4-benzoquinon in 40 ml of methanol added dropwise in about 5 minutes. The stirring was further continued for 10 minutes at 0° C and then 5.60 ml of triethylamine was added to the reaction mixture, which was condensed to about 50 ml under a reduced pressure. Three to four hundred ml of chloroform were added to the mixture and the mixture was washed three times with water, dried over anhydrous magnesium sulfate and the solvent was removed under a reduced pressure. The residue was extracted with ether, extract condensed and n-hexane was added to afford a precipitate, which was collected by filtration to give 13.03g of dicyclohexylammonium 7α-methoxy-7β-(4-hydroxy-3,5-di-tert.-butylbenzylideneamino)-3-acetoxymethyl-3-cephem-4-carboxylate as a yellow powder. A pure sample of this salt with a melting point at 139°–141° C was obtained by crystallization from a mixture of chloroform and n-hexane.

UV spectrum $\lambda_{max}^{THF}$ 283 nm
NMR spectrum (CDCl$_3$) δ ppm:
 8.38 (singlet, —CH=N—)
 7.57 (singlet, benzene ring-H)
 5.52 (broad, OH)
 4.96 (singlet, H at 6-position)
 4.87 (singlet, —CH$_2$— at 3-position)
 3.47 (singlet, —OCH$_3$)
 3.23 (doublet of doublet, H$_2$ at 2-position)
 1.92 (singlet, CH$_3$CO)
 1.40 (singlet, C(CH$_3$)$_3$)

Thin layer chromatography (silica gel):
Developing solvent: chloroform:methanol=4:1
$R_f = 0.74$

| Elementary analysis for C$_{38}$H$_{57}$N$_3$O$_7$S · ½ C$_6$H$_{14}$ | | | |
|---|---|---|---|
| C | H | N | S |
| Calculated: 66.29; | 8.68; | 5.66; | 4.31 |
| Found: 66.12; | 8.64: | 5.70; | 4.20 |

EXAMPLE 2

Dicyclohexylammonium 7α-methxoy-7β-(4-hydroxy-3,5-di-tert.-butylbenzylideneamino)-3-(1-methyl-1H-terazol-5-yl)thiomethyl-3-carboxylate To a solution cooled to −15° C of 1.45g of dicyclohexylammonium 7β-(4-hydroxy-3,5-di-tert.-butylbenzylideamino)-3-(1-methyl-1H-terazol-5-yl)thiomethyl-3-cephem-4-carboxylate in 20 ml of methanol, a solution of 475 mg of 2,3-dichloro-5,6-dicyano-1,4-benzoquinone in 4 ml of methanol was added in dropwise manner. After the addition was completed, the reaction mixture was stirred for 10 minutes at −15° C, then 100 mg of 2,6-di-tert.-butyl-p-cresol was added, and stirring was further continued at 0° C for 10 minutes. Addition of 0.56 ml of triethylamine was made to the resulting reaction mixture, which was then condensed to about 10 ml, 5 ml of chloroform was added thereto and it was washed four times with the same volume of water.

After drying over anhydrous sodium sulfate, the solvent was removed under a reduced pressure and the residue was extracted with a mixture of chloroformether (3:7). The extract was concentrated and a large excess of n-hexane was added to give a precipitate, which was collected by filtration affording 926 mg of dicyclohexylammonium 7α-methoxy-7β-(4-hydroxy-3,5-di-tert.-butylbenzylideneamino)-3-(1-methyl-1H-tertrazol-5-yl)thiomethyl-3-cephem-4-carboxylate as a yellow powder.

UV spectrum $\lambda_{max}^{THF}$ 285 nm
NMR spectrum (CDCl$_3$) δ ppm:
 8.47 (singlet, —CH=N—)
 7.61 (singlet, benzene ring-H)
 5.60 (braod, OH)
 4.98 (singlet, H at 6-position)
 4.42 (singlet, —CH$_2$— at 3-position)
 3.80 (singlet, N—CH$_3$)
 3.48 (singlet, OCH$_3$)
 around 3.4 (doublet, H$_2$ at 2-position)
 1.35 (singlet, C(CH$_3$)$_3$)

Thin layer chromatography (silica gel):
Developing solvent: chloroform:methyanol=4:1
$R_f = 0.72$

EXAMPLE 3

Tert.-ocytlammonium 7α-methoxy-7β-(4-hydroxy-3,5-di-tert.-butylbenzylideneamino)-3-methyl-3-cephem-4-carboxylate A solution cooled to 5°–10° C of 1.67g of tert.-ocylammonium 7β-(4-hydroxy-3,5-di-tert.-butylbenzylideneamino)-3-methyl-3-cephem-4-carboxylate in 150 ml of methanol was added to 0.70g of 2,3-dichloro-5,6-dicyano-1,4-benzoquinone and stirred for 30 minutes at room temperature. The reaction mixture was condensed to dryness under a reduced pressure, the residue dissolved in 100 ml of ethyl acetate, and the resulting solution was washed successively with aqueous 5% sodium hydrogen carbonate and water and dried over anhydrous sodium sulfate. Removal of the solvent under a reduced pressure gave 0.54g of tert.-octylammonium 7α-methoxy-7β-(4-hydroxy-3,5-di-tert.-butylbenzylideneamino)-3-methyl3-cephem-4-carboxylate.

NMR spectrum (CDCl$_3$) δ ppm:
 8.23 (singlet, —CH=N—)
 7.50 (singlet, benzene ring-H)
 5.05 (singlet, H at 6-position)
 3.42 (singlet, OCH$_3$)

EXAMPLE 4

Trimethylbenzylammonium 7α-methoxy-7β-(4-hydroxy-3,5-di-tert.-butylbenzylideneamino)-3-acetoxymethyl-3cephem-4-carboxylate By using 3.185g of trimethylbenzylammonium 7β-(4-hydroxy-3,5-di-tert.-butylbenzylideneamino)-3-acetoxymethyl-3-cephem-4-carboxylate as a starting material, the same reagents and the same procedures as described in example 2, there was obtained 2.56g of trimethylbenzylammonium 7α-methoxy-7β-(4-hydroxy-3,5-di-tert.-butylbenzylideneamino)-3-acetoxymethyl-b 3-cephem-4-carboxylate.

UV spectrum $\lambda_{max}^{THF}$ 284 nm

EXAMPLE 5

Sodium 7α-methoxy-7β-(4-hydroxy-3,5-di-tert.-butylbenzylideneamino)-3-acetoxymethyl-3-cephem-4-carboxylate To a solution chilled to −50° C of 400 mg of sodium 7β-(4-hydroxy-3,5-di-tert.-butylbenzylideneamino)-3-acetoxymethyl-3-cephem-4-carboxylate in 8 ml of anhydrous tetrahydrofuran and 4 ml of methanol, 1 ml of methanolic solution of 20 mg of metallic sodium was added dropwise and subsequently added 110 mg of tert.-butylhypochlorite was added. The resulting mixture was stirred for 30 minutes under cooling and the solvent was removed at room temperature to leave 350 mg of sodium 7α-methoxy-7β-(4-hydroxxy-3,5-di-tert.-butylbenzylideneamino)-3-acetoxymethyl-3-cephem-4-carboxylate.

NMR spectrum (DMSO—d$_6$) δ ppm:
 8.40 (broad singlet, —CH=N—)

7.61 (singlet, benzene ring-H)
5.25 (singlet, H at 6-position)
4.80 (quartet, CH$_2$— at 3 position)
3.46 (singlet, OCH$_3$ at 7-position)
3.41 (quartet, H$_2$ at 2-position)
2.00 (singlet, CH$_3$CO)
1.38 (singlet, C(CH$_3$)$_3$)

EXAMPLE 6

Lithium 7α-methoxy-7β-(4-hydroxy-3,5-di-isopropylbenzylideneamiho)-3-acetoxymethyl-3-cephem-4-carboxylate To a solution chilled to −40° C of 467 mg of lithium 7β-(4-hydroxy-3,5-di-isopropylbenzylideneamino)-3-acetoxymethyl-3-cephe-4carboxylate in 10 ml of anhydrous tetrahydrofuran was added 3 ml of methanol containing mg of dissolved metallic lithium and subsequently 130 mg of tert.-butylhypochlorite was added. The resulting mixture was stirred for 40 minutes under cooling and concentrated to dryness to give lithium 7α-methoxy-7β-(4-hydroxy-3,5-di-isopropylbenzylideneamino)-3-acetoxymethyl-3cephem-4-carboxylate. Purification of the cephem compound thus obtained by a column chromatography using dried silica gel as an adsorbent and a mixture of chloroform - methanol (9:1) as a developing solvent gave 70 mg of a pure sample NMR spectrum (DMSO—d$_6$—CDCl$_3$) δ ppm:
8.48 (singlet, —CH=N—)
7.55 (singlet, benzene ring-H)
5.08 (singelt, H at 6 position)
5.03 (broad singlet, —CH$_2$ at 3-position)
3.57 (singlet, OCH$_3$)
3.05–3.65 (multiplet, H$_2$ at 2-position and 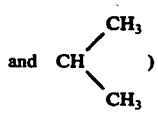

2.07 (singlet, CH$_3$CO)

1.27 (doublet, 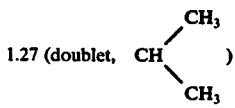

Thin layer chromatography (silica gel):
Developing solvent: chloroform-methanol = 3:1
R$_f$=0.44

EXAMPLE 7

Lithium 7α-methoxy-7β-(4-hydroxy-3,5-di-tert.-butylbenzylideneamino)-3-methyl-3-cephem-4-carboxylate To a solution chilled to −40° C of 436 mg of lithium 7β-(4-hydroxy-3,5-di-tert.-butylbenzylideneamino)-3-methyl-3-cephem-4-carboxylate (prepared by the method described in referential example 2) in 10 ml of anhydrous tetrahydrofuran, 3 ml of methanol containing 7 mg of dissolved metallic lithium was added, and subsequently a solution of 190 mg of N-bromosuccinimide in 2 ml of tetrahydrofuran was added. The resulting reaction mixture was stirred for 30 minutes and then condensed at room temperature. The residue was purified by a column chromotography using dried silica gel as an adsorbent and a mixture of methanol - chloroform (1:9) as a developing solvent to give 200 mg of lithium 7α-methoxy-7β-(4-hydroxy-3,5-di-tert.-butylbenzylideneamino)-3-methyl-3-cephem-4-carboxylate as a pale yellow powder.

NMR spectrum (DMSO—d$_6$) δ ppm:
8.42 (singlet, —CH=N—)
7.58 (singlet, benzene ring-H)
5.05 (singlet, H at 6-position)
3.45 (singlet, OCH$_3$ at 7-position)
3.42 (quartet, H$_2$ at 2-position)
2.10 (singlet, CH$_3$ at 3-position)
1.38 (singlet, —C(CH$_3$)$_3$)

EXAMPLE 8

Lithium 7α-methoxy-7β-(4-hydroxy-3,5-di-tert.-butylbenzylideneamino)-3-methyl-3-cephem-4-carboxylate A solution of 436 mg of lithium 7β-(4-hydroxy-3,5-di-tert.-butylbenzylideneamino)-3-methyl-3-cephem-4-carboxylate in 10 ml of anhydrous tetrahydrofuran was added with 1g of lead dioxide under stirring and ice-cooling. After stirring was continued for 20 minutes, insoluble substances which formed were removed by filtration, 10 ml of methanol was added to the filtrate and the solution was allowed to stand at room temperature for 2 hours. The solvent was removed and the residue was purified by a column chromatography using dried silica gel as an adsorbent and a mixture of methanol - chloroform (1:9) as a developing solvent to give 100 mg of the desired compound, which exhibited an identical NMR spectrum with that of the sample prepared in the above-described example 7.

EXAMPLE 9

Trimethylbenzylammonium 7α-methoxy-7β-(4-hydroxy-3,5-di-tert.-butylbenzylideneamino)-3-(1-methyl-1H-tetrazol-5-yl)thiomethyl-3-cephem-4-carboxylate A solution of 2.17g of trimethylbenzylammonium 7β-(4-hydroxy-3,5-di-tert.-butylbenzylideneamino)-3-(1-methyl-1H-tetrazol-5-yl)thiomethyl-3-cephem-4-carboxylate in 13 ml of methaol and 13 ml of tetrahydrofuran was stirred and chilled in a bath of dry-ice and ethanol. To this solution was added 4 ml of methanol containing 42 mg of dissolved metallic lithium, and subsequently a solution of 780 mg of tert.-butylhypochlorite in 2 ml of dichlorethane was added dropwise. Stirring was continued for 35 minutes under cooling and the reaction mixture was condensed to about 5 ml at room temperature and then about 50 ml of chloroform was added. The mixture was washed four times with aqueous sodium chloride solution, dried over anhydrous magnesium sulfate, and condensed to about 5 ml. Cyclohexane was added to the residue and condensed again to give 1.5g of trimethylbenzylammonium 7α-methoxy-7β-(4-hydroxy-3,5-di-tert.-butylbenzulidenamino)-3-(1-methyl-1H-tetrazol-5-yl)-thiomethyl-3-cephem-4-carboxylate as a pale yellow powder.
thin layer chromatography (silica gel):
Developing solvent: chloroform:methanol=3:1
R$_f$=0.53
What is claimed is:

1. A process for the preparation of 7β-benzylideneamino-7α-alkoxy-3-cephem compounds having the formula

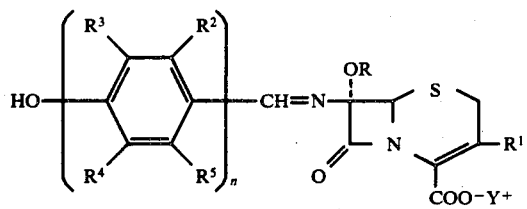

wherein R represents an alkyl group having 1-4 carbon atoms, R¹ represents a hydrogen atom, methyl group, cyanomethyl group, an acyloxymethyl group, carbamoyloxymethyl group, an alkoxymethyl group, an alkylthiomethyl group or a heterocyclic thiomethyl group selected from the group consisting of 2-pyridylthiomethyl, 1-methyl-1H-tetrazol-5-ylthiomethyl, 2-(1,3,5-triazolo)thiomethyl, 2-pyrazolothiomethyl, 1-imidazolinylthiomethyl and 5-methyl-1,3,4-thiadiazolyl-2-thiomethyl, R², R³, R⁴ and R⁵ are the same or different and each represents a hydrogen atom or a straight or branched alkyl group having 1-4 carbon atoms, $n$ is an integer of 1 or 2 and Y⁺ is a cation selected from the group consisting of an alkali metal ion and an ammonium ion having the formula

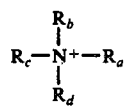

wherein $R_a$, $R_b$, $R_c$ and $R_d$ can be the same of different and each represents, a hydrogen atom, a straight or branched alkyl group having 1-8 carbon atoms, a cycloalkyl group having 5-7 carbon atoms, phenyl group or a phenylalkyl group having 1-4 carbon atoms in the alkyl moiety, or $R_a$ and $R_b$ can be linked together with N to form a saturated heterocyclic ring selected from the group consisting of pyrrolidine, piperidine and morpholine, or $R_a$, $R_b$ and $R_c$ can be linked together with the N atom thereof to form a heteroaromatic ring selected from the group consisting of pyridine, picoline, lutidine, quinoline, quinaldine and pyrimidine, which comprises oxidizing a 7-benzylideneamino-3-cephem compound having the formula

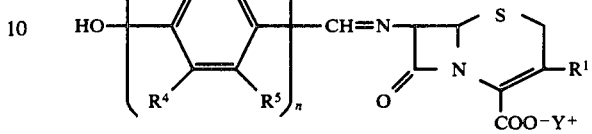

wherein R¹, R², R³, R⁴, R⁵, n and Y⁺ are as defined above with an oxidizing agent selected from the group consisting of lead dioxide, manganese dioxide, dicyanodichlorobenzoquinone, tert.-butylhypochlorite, N-bromosuccinimide and N-chlorosuccinimide, and contacting the resulting oxidation product with an alkanol having 1-4 carbon atoms.

2. The process of claim 1 in which R is methyl, R¹ is methyl, lower-alkanoyloxymethyl or 1-lower alkyl-substituted tetrazol-5-ylthiomethyl, R² and R⁵ are hydrogen, R³ and R⁴ are isopropyl or tert.-butyl, $n$ is 1 and Y⁺ is sodium, lithium, tert.-butylammonium, tert.-octylammonium, dicyclohexylammonium, diisopropylammonium, triethylammonium or trimethylbenzylammonium ion.

3. The process of claim 1 in which the oxidizing agent is lead dioxide.

4. The process of claim 1 in which the oxidizing agent is dicyanodichloquinone.

5. The process of claim 1 in which the oxidizing agent is tert.-butylhypochlorite.

6. The process of claim 1 in which the oxidizing agent is N-bromosuccinimide or N-chlorsuccinimide.

7. The process of claim 1 in which the oxidation and the alkoxylation are performed simultaneously in one step by using dicyanodichlorbenzoquinone, tert.-btylhypochlorite, N-bromosuccinimide or N-chlorsuccinimide as the oxidizing agent.

* * * * *

UNITED STATES PATENT AND TRADEMARK OFFICE
CERTIFICATE OF CORRECTION

PATENT NO. : 4,048,155
DATED : September 13, 1977
INVENTOR(S) : HIROAKI YANAGISAWA et al It is certified that error appears in the above-identified patent and that said Letters Patent are hereby corrected as shown below:

Column 1, line 7: replace "cepehm" with ---cephem---.

Column 1, line 29: before "alkoxy-", replace "a" with ---an---.

Column 1, line 46: replace "thiadiaolyl" with ---thiadiazolyl---.

Column 2, line 36: replace "7-banzylideneamino" with ---7-benzylideneamino---.

Column 2, line 44: before "difficulties", replace "of" with ---or---.

Column 3, line 27: replace "N-bormosuccinimide" with ---N-bromosuccinimide---.

Column 4, line 14: replace "alknaol" with ---alkanol---.

Column 5, line 17: replace "Rhu 1" with ---$R^1$---.

Column 6, line 7: replace "cemphem" with ---cephem---.

Column 6, line 41: replace "chlorform" with ---chloroform---.

Column 6, line 45: replace "methyoxy" with ---methoxy---.

UNITED STATES PATENT AND TRADEMARK OFFICE
CERTIFICATE OF CORRECTION

PATENT NO. : 4,048,155
DATED : September 13, 1977
INVENTOR(S) : HIROAKI YANAGISAWA et al It is certified that error appears in the above-identified patent and that said Letters Patent are hereby corrected as shown below:

Column 6, line 53: replace "benzoquinon" with ---benzoquinone---.

Column 7, line 28: replace "methxoy" with ---methoxy---.

Column 7, line 34: replace "benzylideamino" with ---benzylideneamino---.

Column 7, line 54: replace "tertrazol" with ---tetrazol---.

Column 7, line 61: replace "braod" with ---broad---.

Column 8, line 2: replace "methyanol" with ---methanol---.

Column 8, line 10: replace "ocylammonium" with ---octylammonium---.

Column 8, line 22: rewrite "-methyl3-" as --- -methyl-3- ---

Column 8, line 35: rewrite "-3cephem-" as --- -3-cephem- ---.

Column 8, line 43: before "3-cephem-", delete "b".

Column 8, line 63: replace "hydroxxy" with ---hydroxy---.

Column 9, line 16: replace "cephe-4carboxylate" with ---cephem-4-carboxylate---.

UNITED STATES PATENT AND TRADEMARK OFFICE
CERTIFICATE OF CORRECTION

PATENT NO. : 4,048,155
DATED : September 13, 1977
INVENTOR(S) : HIROAKI YANAGISAWA et al It is certified that error appears in the above-identified patent and that said Letters Patent are hereby corrected as shown below:

Column 9, line 18: before "mg", insert ---7---.

Column 9, line 40: replace "CH$<^{CH_3}_{CH_3}$" with ---C$\underline{H}<^{CH_3}_{CH_3}$---.

Column 9, line 46: replace "CH$<^{CH_3}_{CH_3}$" with ---CH$<^{C\underline{H}_3}_{C\underline{H}_3}$---.

Column 10, line 47: replace "methaol" with ---methanol---.

Column 10, line 62: replace "zulidenamino" with ---zylidenamino---.

Column 12, Claim 4, line 2: replace "dicyanodichloquinone" with ---dicyanodichloroquinone---.

Signed and Sealed this

Eighteenth Day of September 1979

[SEAL]

Attest:

LUTRELLE F. PARKER

Attesting Officer    Acting Commissioner of Patents and Trademarks